(12) United States Patent
Banisakher et al.

(10) Patent No.: US 11,494,418 B2
(45) Date of Patent: Nov. 8, 2022

(54) SYSTEMS AND METHODS FOR DETERMINING DOCUMENT SECTION TYPES

(71) Applicants: Deya Banisakher, Miami, FL (US);
Naphtali Rishe, Miami, FL (US);
Mark Finlayson, North Bay Village, FL (US)

(72) Inventors: Deya Banisakher, Miami, FL (US);
Naphtali Rishe, Miami, FL (US);
Mark Finlayson, North Bay Village, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 105 days.

(21) Appl. No.: 17/160,712

(22) Filed: Jan. 28, 2021

(65) Prior Publication Data
US 2022/0237210 A1    Jul. 28, 2022

(51) Int. Cl.
| | | |
|---|---|---|
| G06F 16/00 | (2019.01) | |
| G06F 16/28 | (2019.01) | |
| G06F 17/18 | (2006.01) | |
| G16H 15/00 | (2018.01) | |
| G06N 20/00 | (2019.01) | |
| G16H 10/60 | (2018.01) | |
| G06F 7/14 | (2006.01) | |

(52) U.S. Cl.
CPC .............. *G06F 16/285* (2019.01); *G06F 7/14* (2013.01); *G06F 17/18* (2013.01); *G06N 20/00* (2019.01); *G16H 10/60* (2018.01); *G16H 15/00* (2018.01)

(58) Field of Classification Search
CPC .......... G06F 16/285; G06F 7/14; G06F 17/18; G06N 20/00; G16H 10/60; G16H 15/00
See application file for complete search history.

(56) References Cited

U.S. PATENT DOCUMENTS

| | | | |
|---|---|---|---|
| 7,685,083 B2* | 3/2010 | Fairweather | G06K 13/0825 706/45 |
| 9,535,974 B1* | 1/2017 | Kesin | G06F 40/106 |
| 10,191,975 B1 | 1/2019 | Eisenberg et al. | |
| 10,410,294 B1* | 9/2019 | Chatman | G06Q 40/12 |
| 10,789,543 B1* | 9/2020 | Sun | G06N 20/00 |
| 10,839,161 B2* | 11/2020 | Galitsky | G06F 40/216 |
| 11,176,027 B1* | 11/2021 | Xiao | G06F 11/3684 |
| 11,200,412 B2* | 12/2021 | Tripathi | G06V 30/413 |
| 11,342,055 B2* | 5/2022 | Chang | G16H 20/40 |
| 11,373,424 B1* | 6/2022 | Fleming | G06V 30/416 |
| 2002/0165717 A1* | 11/2002 | Solmer | G10L 15/197 704/256.4 |
| 2004/0059736 A1* | 3/2004 | Willse | G06F 40/20 |
| 2007/0124200 A1* | 5/2007 | Simons | G06Q 30/02 705/14.6 |

(Continued)

*Primary Examiner* — Noosha Arjomandi
(74) *Attorney, Agent, or Firm* — Saliwanchik, Lloyd & Eisenschenk

(57) ABSTRACT

Systems and methods for discovering and/or determining section types for a given document class in a data-driven manner are provided. A modified Bayesian model merging algorithm can be used, along with extending an Analogical Story Merging (ASM) algorithm. The systems and methods can learn the section structure of documents without a pre-existing ontology of sections or time-intensive annotation efforts.

18 Claims, 9 Drawing Sheets

(56) References Cited

U.S. PATENT DOCUMENTS

| | | | | |
|---|---|---|---|---|
| 2007/0124202 | A1* | 5/2007 | Simons | G06Q 30/0241 |
| | | | | 705/346 |
| 2010/0293451 | A1* | 11/2010 | Carus | G06F 16/36 |
| | | | | 715/256 |
| 2011/0191274 | A1* | 8/2011 | Yu | G06N 5/02 |
| | | | | 706/46 |
| 2012/0296891 | A1* | 11/2012 | Rangan | G06F 16/3347 |
| | | | | 707/E17.014 |
| 2012/0330869 | A1* | 12/2012 | Durham | G06N 5/022 |
| | | | | 706/16 |
| 2013/0311462 | A1* | 11/2013 | Khan | G06F 16/3344 |
| | | | | 707/728 |
| 2016/0026622 | A1* | 1/2016 | Bunin | G06F 16/367 |
| | | | | 704/9 |
| 2017/0337268 | A1* | 11/2017 | Ait-Mokhtar | G06F 16/3344 |
| 2018/0039907 | A1* | 2/2018 | Kraley | G06V 10/82 |
| 2018/0097826 | A1* | 4/2018 | Luan | H04L 63/1416 |
| 2020/0081980 | A1 | 3/2020 | Eisenberg et al. | |
| 2020/0134024 | A1 | 4/2020 | Banisakher et al. | |
| 2021/0056300 | A1* | 2/2021 | Chitta | G06V 30/416 |
| 2021/0090694 | A1* | 3/2021 | Colley | G16B 40/00 |
| 2021/0124919 | A1* | 4/2021 | Balakrishnan | G06V 30/245 |
| 2021/0224695 | A1* | 7/2021 | Stefanov | G06V 30/40 |
| 2021/0271699 | A1* | 9/2021 | Smith | G06F 16/316 |
| 2021/0326744 | A1* | 10/2021 | Israel | G06N 20/00 |
| 2021/0390573 | A1* | 12/2021 | Reedy | G06N 20/00 |
| 2022/0012426 | A1* | 1/2022 | Ziemer | G06F 16/248 |
| 2022/0180745 | A1* | 6/2022 | Banaei-Kashani | G08G 1/093 |

* cited by examiner

| Corpus | Document Class | # of Docs. | # of Secs. | Secs. / Doc. | Words / Doc. |
|---|---|---|---|---|---|
| 1 | Psychiatric Evaluations | 150 | 2,824 | 18.8 | 1,521 |
| 2 | Discharge Summaries | 150 | 2,977 | 19.8 | 1,829 |
| 3 | Radiology Reports | 423 | 2,538 | 6.0 | 463 |
| 4 | U.S. Patents | 464 | 3,249 | 7.0 | 18,351 |

FIG. 2

| # | Section | % Present | P | R | $F_1$ |
|---|---|---|---|---|---|
| | GENERAL PATIENT INFO | | | | |
| 1 | IDENTIFYING DATA | 100 | 0.96 | 0.96 | 0.96 |
| 2 | CHIEF COMPLAINT | 100 | 0.94 | 0.92 | 0.93 |
| | MDEICAL HISTORY | | | | |
| 3 | HIST. OF PRSNT. ILLNSS. | 95 | 0.96 | 0.94 | 0.95 |
| 4 | PSYCHIATRIC HISTORY | 82 | 0.89 | 0.89 | 0.89 |
| 5 | SUBST. ABUSE HIST. | 88 | 0.90 | 0.88 | 0.89 |
| 6 | REVIEW OF SYMPTOMS | 96 | 0.95 | 0.95 | 0.95 |
| 7 | SURGERIES | 33 | 0.80 | 0.71 | 0.75 |
| 8 | ALLERGIES | 98 | 0.92 | 0.94 | 0.93 |
| 9 | CURRENT MEDICATIONS | 100 | 0.94 | 0.90 | 0.92 |
| | FAMILY HISTORY | | | | |
| 10 | BIRTH AND DVLP. HIST. | 31 | 0.73 | 0.67 | 0.70 |
| 11 | ABUSE HIST. / TRAUMA | 79 | 0.90 | 0.86 | 0.88 |
| 12 | FAMILY PSYCH. HIST. | 73 | 0.92 | 0.90 | 0.91 |
| 13 | FAMILY MED. HISTORY | 92 | 0.95 | 0.93 | 0.94 |
| 14 | SOCIAL HISTORY | 76 | 0.90 | 0.88 | 0.89 |
| 15 | PREGNANCY | 47 | 0.75 | 0.69 | 0.72 |
| 16 | SPIRITUAL BELIEFS | 24 | 0.72 | 0.68 | 0.70 |
| 17 | EDUCATION | 68 | 0.83 | 0.77 | 0.80 |
| 18 | EMPLOYMENT | 79 | 0.88 | 0.86 | 0.87 |
| 19 | LEGAL | 20 | 0.74 | 0.65 | 0.69 |
| | MENTAL STATUS | | | | |
| 20 | MENTAL STATUS | 95 | 0.95 | 0.91 | 0.93 |
| 21 | STRENGTHS AND SUPPORTS | 71 | 0.85 | 0.83 | 0.84 |
| | TREATMENT | | | | |
| 22 | FORMULATION | 62 | 0.83 | 0.79 | 0.81 |
| 23 | DIAGNOSES | 100 | 0.97 | 0.95 | 0.96 |
| 24 | PROGNOSIS | 74 | 0.85 | 0.83 | 0.84 |
| 25 | TREATMENT PLAN | 100 | 0.95 | 0.89 | 0.92 |
| | | Average | 0.88 | 0.85 | 0.86 |

FIG. 3

| # | Section | % Present | P | R | $F_1$ |
|---|---|---|---|---|---|
| | CLINICAL INFORMATION | | | | |
| 1 | CLINICAL HISTORY | 100 | 0.96 | 0.92 | 0.94 |
| | EXAM DETAILS | | | | |
| 2 | EXAM | 100 | 0.92 | 0.92 | 0.92 |
| 3 | COMPARISON | 86 | 0.84 | 0.76 | 0.80 |
| 4 | CONTRAST | 14 | 0.71 | 0.65 | 0.68 |
| 5 | PROCEDURE | 100 | 0.91 | 0.89 | 0.90 |
| | FINDINGS | | | | |
| 6 | FINDINGS | 100 | 0.89 | 0.83 | 0.86 |
| | IMPRESSION | | | | |
| 7 | IMPRESSION | 100 | 0.90 | 0.84 | 0.87 |
| 8 | ATTENDING STATEMENT | 0 | - | - | - |
| | Average | | 0.88 | 0.83 | 0.85 |

FIG. 4

| # | Section | % Present | P | R | $F_1$ |
|---|---|---|---|---|---|
| | GENERAL PATIENT INFO | | | | |
| 1 | ADMIT | 100 | 0.95 | 0.91 | 0.93 |
| 2 | DISCHARGE | 100 | 0.95 | 0.91 | 0.93 |
| 3 | SERVICE | 100 | 0.91 | 0.91 | 0.91 |
| | PROVIDER INFO | | | | |
| 4 | ATTENDING | 82 | 0.82 | 0.82 | 0.82 |
| 5 | ADMITTING | 100 | 0.75 | 0.77 | 0.76 |
| 6 | DISCHARGING | 100 | 0.80 | 0.74 | 0.77 |
| | CONDITION BEFORE ADMISSION | | | | |
| 7 | ADMISSION DIAGNOSES | 100 | 0.90 | 0.82 | 0.86 |
| 8 | HISTORY | 76 | 0.90 | 0.81 | 0.85 |
| 9 | MEDICATIONS | 100 | 0.83 | 0.81 | 0.82 |
| 10 | REASON FOR ADMISSION | 100 | 0.80 | 0.78 | 0.79 |
| | CONDITION AT DISCHARGE | | | | |
| 11 | CONDITION | 100 | 0.78 | 0.76 | 0.77 |
| 12 | DISPOSITION | 34 | 0.65 | 0.71 | 0.68 |
| 13 | DISCHARGE DIAGNOSES | 89 | 0.85 | 0.83 | 0.84 |
| 14 | OTHER DIAGNOSES | 0 | - | - | - |
| 15 | PHYSICAL EXAM ON DISCH. | 40 | 0.84 | 0.84 | 0.84 |
| | MEDICAL HISTORY | | | | |
| 16 | ALLERGIES | 100 | 0.85 | 0.79 | 0.82 |
| 17 | FAMILY HISTORY | 43 | 0.82 | 0.80 | 0.81 |
| 18 | GYNECOLOGICAL HISTORY | 0 | - | - | - |
| 19 | PAST MEDICAL HISTORY | 100 | 0.81 | 0.83 | 0.82 |
| 20 | PAST SURGICAL HISTORY | 100 | 0.88 | 0.84 | 0.86 |
| 21 | SOCIAL HISTORY | 37 | 0.77 | 0.75 | 0.76 |
| | HOSPITAL COURSE | | | | |
| 22 | CONSULTATION | 6 | 0.64 | 0.64 | 0.64 |
| 23 | HOSPITAL COURSE | 85 | 0.89 | 0.85 | 0.87 |
| 24 | PHYSICAL | 28 | 0.79 | 0.77 | 0.78 |
| 25 | PROCEDURES | 65 | 0.84 | 0.82 | 0.83 |
| 26 | STUDIES | 0 | - | - | - |
| | DISCHARGE INSTRUCTIONS | | | | |
| 27 | FOLLOW UP | 0 | - | - | - |
| 28 | DIAGNOSTIC STUDIES RECD | 0 | - | - | - |
| 29 | DISCHARGE INSTRUCTIONS | 100 | 0.92 | 0.92 | 0.92 |
| 30 | DISCHARGE MEDICATIONS | 100 | 0.91 | 0.93 | 0.91 |
| | Average | | 0.83 | 0.81 | 0.82 |

FIG. 5

| # | Section | % Present | P | R | $F_1$ |
|---|---|---|---|---|---|
| 1 | TECHNICAL FIELD | 100 | 0.87 | 0.83 | 0.85 |
| 2 | BACKGROUND ART | 100 | 0.93 | 0.89 | 0.91 |
| 3 | SUMMARY OF THE INVENTION | 100 | 0.94 | 0.92 | 0.93 |
| 4 | DESCRIPTION OF DRAWINGS | 100 | 0.96 | 0.94 | 0.95 |
| 5 | PREFERRED EMBODIMENTS | 100 | 0.96 | 0.96 | 0.96 |
| 6 | INDUSTRIAL APPLICABILITY | 41 | 0.85 | 0.72 | 0.78 |
| 7 | EXAMPLES | 16 | 0.80 | 0.71 | 0.75 |
| | | Average | 0.90 | 0.85 | 0.88 |

FIG. 6

| Algorithm | Psyc. | Disch. | Rad. | Pat. |
|---|---|---|---|---|
| NMF | 0.40 | 0.39 | 0.43 | 0.42 |
| *tf-idf*+K-means | 0.47 | 0.40 | 0.52 | 0.49 |
| LDA+K-means | 0.50 | 0.41 | 0.54 | 0.51 |
| Our Approach | | | | |
| Lexical Only | 0.74 | 0.72 | 0.77 | 0.81 |
| Semantic+Lexical | 0.80 | 0.75 | 0.78 | 0.83 |
| Positional+Lexical | 0.84 | 0.80 | 0.81 | 0.85 |
| All_Features_No Header | 0.87 | 0.83 | 0.85 | 0.87 |
| Section Merging_ALL | 0.89 | 0.85 | 0.87 | 0.93 |

FIG. 7

| Corpus | P | R | $F_1$ |
|---|---|---|---|
| Psychiatric Evaluations | 0.87 | 0.92 | 0.89 |
| Discharge Summaries | 0.83 | 0.88 | 0.85 |
| Radiology Reports | 0.87 | 0.91 | 0.89 |
| US Patents | 0.94 | 0.96 | 0.95 |

FIG. 8

| Section | Header | # Words | # Sent. | Sent. Length | % Present |
|---|---|---|---|---|---|
| | GENERAL PATIENT INFO | | | | |
| 1 | IDENTIFYING DATA | 12 | 2 | 6 | 100 |
| 2 | CHIEF COMPLAINT | 27 | 3 | 9 | 100 |
| | MEDICAL HISTORY | | | | |
| 3 | HIST. OF PRSNT. ILLNSS. | 232 | 29 | 8 | 95 |
| 4 | PSYCHIATRIC HISTORY | 85 | 8 | 11 | 82 |
| 5 | SUBSTANCE ABUSE HIST. | 98 | 10 | 10 | 88 |
| 6 | REVIEW OF SYMPTOMS | 150 | 19 | 8 | 96 |
| 7 | SURGERIES | 28 | 3 | 7 | 33 |
| 8 | ALLERGIES | 4 | 2 | 2 | 98 |
| 9 | CURRENT MEDICATIONS | 40 | 9 | 4 | 100 |
| | FAMILY HISTORY | | | | |
| 10 | BIRTH AND DEVELOP. HIST. | 59 | 5 | 10 | 31 |
| 11 | ABUSE HIST./TRAUMA | 110 | 9 | 12 | 79 |
| 12 | FAMILY PSYCHIATRIC HIST. | 44 | 5 | 9 | 73 |
| 13 | FAMILY MEDICAL HISTORY | 48 | 7 | 7 | 92 |
| 14 | SOCIAL HISTORY | 80 | 7 | 11 | 76 |
| 15 | PREGNANCY | 29 | 3 | 8 | 47 |
| 16 | SPIRITUAL BELIEFS | 12 | 2 | 5 | 24 |
| 17 | EDUCATION | 32 | 3 | 8 | 68 |
| 18 | EMPLOYMENT | 31 | 3 | 9 | 79 |
| 19 | LEGAL | 10 | 1 | 5 | 20 |
| | MENTAL STATUS | | | | |
| 20 | MENTAL STATUS | 155 | 18 | 9 | 95 |
| 21 | STRENGTHS AND SUPPORTS | 8 | 1 | 8 | 71 |
| | TREATMENT | | | | |
| 22 | FORMULATION | 35 | 4 | 8 | 62 |
| 23 | DIAGNOSES | 63 | 12 | 5 | 100 |
| 24 | PROGNOSIS | 8 | 2 | 3 | 74 |
| 25 | Treatment Plan | 121 | 12 | 10 | 100 |

FIG. 9

| Section | Header | # Words | # Sent. | Sent. Length | % Present |
|---|---|---|---|---|---|
| | GENERAL PATIENT INFO | | | | |
| 1 | ADMIT DATE | 3 | 1 | 3 | 100 |
| 2 | DISCHARGE DATE | 3 | 1 | 3 | 100 |
| 3 | SERVICE | 4 | 2 | 2 | 100 |
| | PROVIDER INFO | | | | |
| 4 | ATTENDING | 2 | 1 | 2 | 82 |
| 5 | ADMIT PHYSICIAN | 2 | 1 | 2 | 100 |
| 6 | DISCHARGE PHYSICIAN | 2 | 1 | 2 | 100 |
| | CONDITION BEFORE ADMISSION | | | | |
| 7 | ADMISSION DIAGNOSES | 96 | 12 | 8 | 100 |
| 8 | HISTORY | 135 | 15 | 9 | 76 |
| 9 | MEDICATIONS | 55 | 11 | 5 | 100 |
| 10 | REASON FOR ADMISSION | 162 | 18 | 9 | 100 |
| | CONDITION AT DISCHARGE | | | | |
| 11 | CONDITION | 4 | 2 | 2 | 100 |
| 12 | DISPOSITION | 2 | 1 | 2 | 34 |
| 13 | DISCHARGE DIAGNOSES | 144 | 18 | 8 | 89 |
| 14 | OTHER DIAGNOSES | - | - | - | 0 |
| 15 | PHYSICAL EXAM ON DISCH. | 45 | 9 | 5 | 40 |
| | MEDICAL HISTORY | | | | |
| 16 | ALLERGIES | 12 | 3 | 4 | 100 |
| 17 | FAMILY HISTORY | 81 | 9 | 9 | 43 |
| 18 | GYNECOLOGICAL HISTORY | - | - | - | 0 |
| 19 | PAST MEDICAL HISTORY | 144 | 16 | 9 | 100 |
| 20 | PAST SURGICAL HISTORY | 32 | 4 | 8 | 100 |
| 21 | SOCIAL HISTORY | 84 | 7 | 12 | 37 |
| | HOSPITAL COURSE | | | | |
| 22 | CONSULTATION | 88 | 11 | 8 | 6 |
| 23 | HOSPITAL COURSE | 168 | 14 | 12 | 85 |
| 24 | PHYSICAL | 66 | 11 | 6 | 28 |
| 25 | PROCEDURES | 15 | 5 | 3 | 65 |
| 26 | STUDIES | - | - | - | 0 |
| | DISCHARGE INSTRUCTIONS | | | | |
| 27 | FOLLOW UP | - | - | - | 0 |
| 28 | DIAGNOSTIC STUDIES RECD | - | - | - | 0 |
| 29 | DISCHARGE INSTRUCTIONS | 408 | 34 | 12 | 100 |
| 30 | DISCHARGE MEDICATIONS | 72 | 12 | 6 | 100 |

FIG. 10

| Section | Header | # Words | # Sent. | Sent. Length | % Present |
|---|---|---|---|---|---|
| | CLINICAL INFORMATION | | | | |
| 1 | CLINICAL HISTORY | 80 | 8 | 10 | 100 |
| | EXAM DETAILS | | | | |
| 2 | EXAM | 16 | 2 | 8 | 100 |
| 3 | COMPARISON | 16 | 2 | 8 | 86 |
| 4 | CONTRAST | 14 | 2 | 7 | 14 |
| 5 | PROCEDURE | 12 | 2 | 6 | 100 |
| | FINDINGS | | | | |
| 6 | FINDINGS | 192 | 24 | 8 | 100 |
| | IMPRESSION | | | | |
| 7 | IMPRESSION | 133 | 19 | 7 | 100 |
| 8 | ATTENDING STATEMENT | - | - | - | 0 |

FIG. 11

| Section | Header | # Words | # Sent. | Sent. Length | % Present |
|---|---|---|---|---|---|
| 1 | TECHNICAL FIELD | 85 | 3 | 8 | 100 |
| 2 | BACKGROUND ART | 267 | 57 | 11 | 100 |
| 3 | SUMMARY OF THE INVENTION | 1,286 | 89 | 10 | 100 |
| 4 | DESCRIPTION OF DRAWINGS | 973 | 19 | 8 | 100 |
| 5 | PREFERRED EMBODIMENTS | 4,106 | 208 | 7 | 100 |
| 6 | INDUSTRIAL APPLICABILITY | 2,731 | 96 | 2 | 31 |
| 7 | EXAMPLES | 1,258 | 82 | 4 | 14 |

FIG. 12

SYSTEMS AND METHODS FOR DETERMINING DOCUMENT SECTION TYPES

BACKGROUND

Many types of documents have an explicit section structure, that is, headers that delimit blocks of the text and set expectations about the content and purpose of that block. Automatically labeling sections with a pre-defined ontology of section types is useful for document understanding and has been shown to improve tasks as varied as information extraction, data mining, and document search. Automatically labeling sections with their types requires not just a list of possible sections, but also what different headers are used for each, their usual order (with possible exceptions), and the type of language normally found within. Also, manually creating this knowledge is laborious and error prone.

BRIEF SUMMARY

In view of the above, there is a need in the art for a solution to automatically discovering the information needed for automatic labeling of documents sections (e.g., automatically discovering from examples). Automatically discovering types of sections is challenging; for a document class (e.g., a psychiatric evaluation or a U.S. Patent), the presence of a particular section type is often ambiguous. First, there is great variety and ambiguity in the section headers; second, sections are sometimes included within other sections; third, the section order might not be strict; and fourth, sections may be omitted for a variety of reasons. Embodiments of the subject invention provide systems and methods for discovering and/or determining section types for a given document class in a data-driven manner. A modified Bayesian model merging algorithm (see Stolcke et al., Inducing probabilistic grammars by bayesian model merging, In International Colloquium on Grammatical Inference, pages 106-118, Springer, 1994; which is hereby incorporated by reference herein in its entirety) can be used, along with extending an Analogical Story Merging (ASM) algorithm (see Finlayson, Inferring propp's functions from semantically annotated text, The Journal of American Folklore, 129(511):55-77, 2016; which is hereby incorporated by reference herein in its entirety). The systems and methods can be used on a wide variety of types of documents, including but not limited to documents in the clinical domain (e.g., psychiatric evaluations, discharge summaries, radiology reports, etc.) and documents in the intellectual property (IP) domain (e.g., U.S. patents, etc.).

In an embodiment, a system for determining section types of a given document class can comprise: a processor; a memory in operable communication with the processor; and a (non-transitory) machine-readable medium in operable communication with the processor and the memory, the machine-readable medium having instructions stored thereon that, when executed by the processor, perform the following steps: receiving a corpus of documents of the given document class; using a modified Bayesian model merging algorithm on the corpus to determine the section types of the given document class; and storing the determined section types on the memory to be used for labeling a document of the given document class. The using of the modified Bayesian model merging algorithm on the corpus can comprise extending an ASM approach with a Bayesian model merging algorithm. The using of the modified Bayesian model merging algorithm on the corpus can comprise: creating an initial Hidden Markov Model (HMM)-like model, where each document of the corpus is represented as a linear chain of states, with each state of the linear chain of states corresponding to a section of unknown type in a same order as found in the respective document of the corpus; performing a merge operation on the initial HMM-like model to merge states and generate an updated model; defining a prior probability distribution (or a "prior") over the updated model; computing a posterior probability distribution based on the prior probability distribution; and searching a merge space of the updated model based on the posterior probability distribution to determine the section types of the given document class. The searching of the merge space of the updated model can comprise maximizing the posterior probability distribution to give a generalizable model that fits the corpus. The computing of the posterior probability distribution can comprise computing $P(M)P(D|M)$, which is proportional to $P(M|D)$, where $P(M)$ is the prior probability distribution, $P(M|D)$ is the posterior probability distribution, M represents the updated model, and D represents a document of the corpus. The defining of the prior probability distribution can comprise using Equations (1) and (2) as defined herein. The similarity threshold (T) can be set as 1.5 standard deviations from a mean similarity of the similarity function; and/or if headers of all sections in the updated model are exactly the same, $G(S_i)$ is set to 1. The corpus of documents can comprise, for example, at least 100 documents (e.g., at least 150 documents). The given document class can be, for example, a psychiatric evaluation, a discharge summary, a radiology report, or a United States patent document.

In another embodiment, a method for determining section types of a given document class can comprise: receiving (e.g., by a processor) a corpus of documents of the given document class; using (e.g., by the processor) a modified Bayesian model merging algorithm on the corpus to determine the section types of the given document class; and storing (e.g., by the processor) the determined section types (e.g., on a memory in operable communication with the processor) to be used for labeling a document of the given document class. The using of the modified Bayesian model merging algorithm on the corpus can comprise extending an ASM approach with a Bayesian model merging algorithm. The using of the modified Bayesian model merging algorithm on the corpus can comprise: creating an initial HMM-like model, where each document of the corpus is represented as a linear chain of states, with each state of the linear chain of states corresponding to a section of unknown type in a same order as found in the respective document of the corpus; performing a merge operation on the initial HMM-like model to merge states and generate an updated model; defining a prior probability distribution over the updated model; computing a posterior probability distribution based on the prior probability distribution; and searching a merge space of the updated model based on the posterior probability distribution to determine the section types of the given document class. The searching of the merge space of the updated model can comprise maximizing the posterior probability distribution to give a generalizable model that fits the corpus. The computing of the posterior probability distribution can comprise computing $P(M)P(D|M)$, which is proportional to $P(M|D)$. The defining of the prior probability distribution can comprise using Equations (1) and (2) as defined herein. The similarity threshold (T) can be set as 1.5 standard deviations from a mean similarity of the similarity function; and/or if headers of all sections in the updated model are exactly the same, $G(S_i)$ is set to 1. The corpus of documents can comprise, for example, at least 100 documents (e.g., at least 150 documents). The given document class can be, for example, a psychiatric evaluation, a discharge summary, a radiology report, or a United States patent document.

BRIEF DESCRIPTION OF DRAWINGS

FIG. 2 is a table showing a summary of corpora statistics.

FIG. 3 is a table showing section ontology for psychiatric evaluations corpus and merging results. Column 3 shows the percentage of documents that contain that section type, and columns 4-6 show the precision (P), recall (R), and F1 scores, respectively, for section merging.

FIG. 4 is a table showing section ontology for radiology reports corpus and merging results. Columns are organized as in FIG. 3.

FIG. 5 is a table showing section ontology for discharge summary corpus and merging results. Statistics are the same as in FIG. 3.

FIG. 6 is a table showing section ontology for description section in U.S. patent documents. Statistics are the same as in FIG. 3.

FIG. 7 is a table showing Rand results for section type discovery of baseline algorithms and a system/method according to an embodiment of the subject invention (labeled "our approach" in FIG. 7). The results from a system/method according to an embodiment of the subject invention are also shown for different combinations of features FIG. 8 is a table showing ordering results for section type discovery.

FIG. 9 is a table showing section ontology for psychiatric evaluation reports and corpus statistics. Statistics include the total number of documents in the corpus, the average number of words per section (#Words), the average number of sentences per document (#Sent.), the average sentence length across the corpus (Sent. Length), and the percentage of sections present across the corpus per section type (% Present).

FIG. 10 is a table showing section ontology for discharge summaries. Statistics are the same as in FIG. 9.

FIG. 11 is a table showing section ontology for radiology reports. Statistics are the same as in FIG. 9.

FIG. 12 is a table showing section ontology for the description section in U.S. patent documents. Statistics are the same as in FIG. 9.

DETAILED DESCRIPTION

Figure 1:
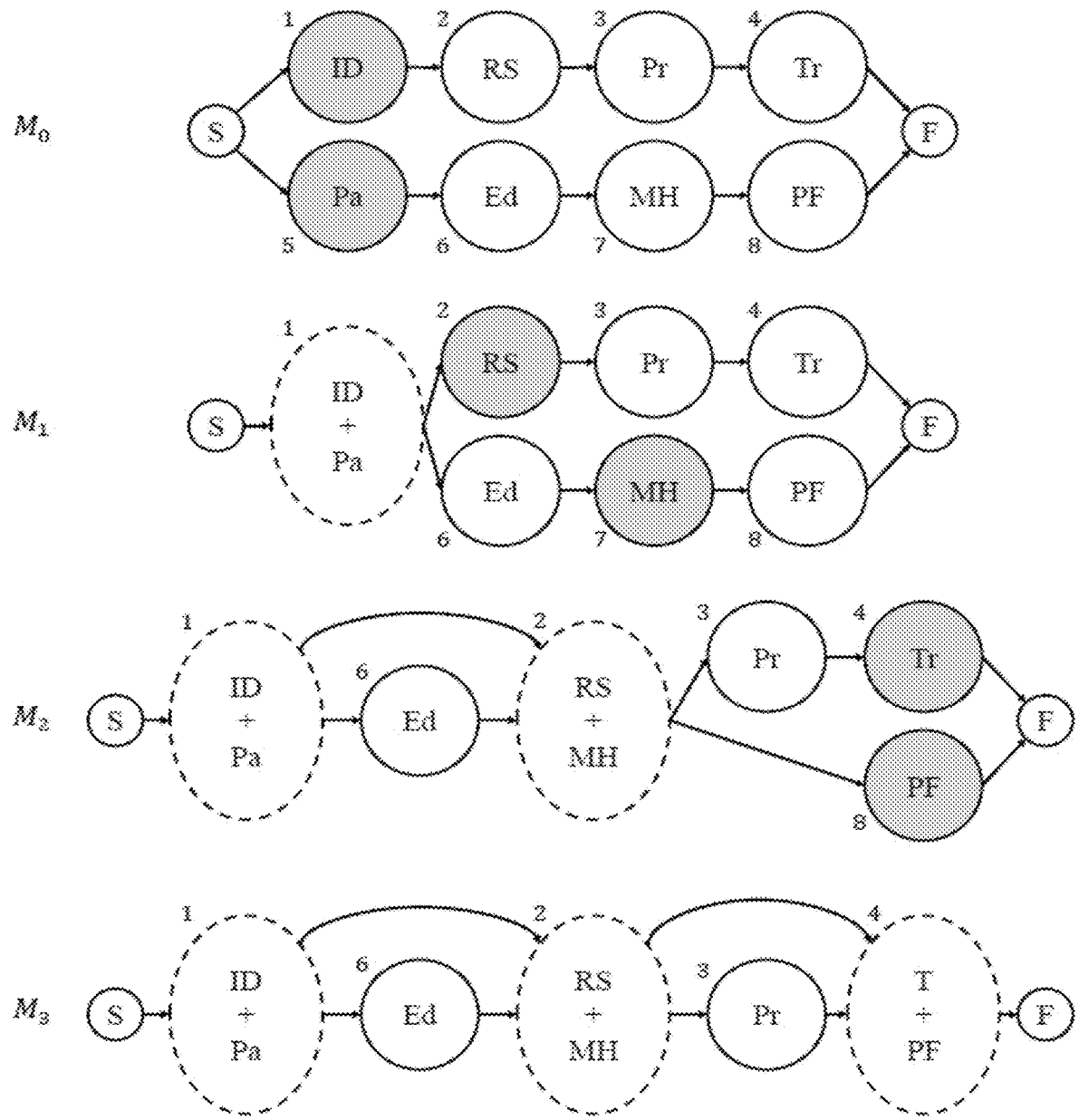
FIG. 1 is a schematic view of a system according to an embodiment of the subject invention, applied to two psychiatric reports D. Each report includes four sections, and states are represented by circles and transitions by arrows. Abbreviated section headings inside states indicate that the state can omit that section content, and shaded states are merged into the dashed state in the next step.

Embodiments of the subject invention provide systems and methods for discovering and/or determining section types for a given document class in a data-driven manner. A modified Bayesian model merging algorithm can be used, along with extending an Analogical Story Merging (ASM) algorithm. The systems and methods can be used on a wide variety of types of documents, including but not limited to documents in the clinical domain (e.g., psychiatric evaluations, discharge summaries, radiology reports, etc.) and documents in the intellectual property (IP) domain (e.g., U.S. patents, etc.). The approach of systems and methods of embodiments of the subject invention advantageously make it feasible to learn the section structure of documents without a pre-existing ontology of sections or time-intensive annotation efforts. The examples show the approach successfully demonstrated on four different corpora (psychiatric evaluations, discharge summaries, radiology reports, and U.S. patents).

As discussed in more detail in the Examples, the approach of systems and methods of embodiments of the subject invention has been texted on four different document classes from two domains: psychiatric evaluations, discharge summaries, and radiology reports in the clinical domain; and U.S. patent documents in the IP domain. Each corpus was paired with ground truth data represented as ontologies of distinct section types found within each corpus. The first author annotated the clinical documents (i.e., corpora 1, 2, 3) along with a clinical domain expert and the patent documents (i.e., corpus 4) along with a computer science undergraduate student. The interrater reliability was calculated using Cohen's κ statistic, achieving 0.85, 0.81, 0.88, and 0.89 for each corpus (psychiatric evaluations, discharge summaries, radiology reports, and U.S. patent documents), respectively. These agreement values are considered "perfect" agreement (see, e.g., Artstein et al., Inter-Coder Agreement for Computational Linguistics, Computational Linguistics, 34(4):555-596, 2008; which is hereby incorporated by reference herein in its entirety). Additionally, the ground truth data was only generated for evaluating the approach. FIG. 2 shows a summary of these corpora and their corresponding section and word statistics. More detailed statistics for each corpus (psychiatric evaluations, discharge summaries, radiology reports, and U.S. patent documents) are provided in FIGS. 9, 10, 11, and 12, respectively. Each corpus will now be described in detail, followed by the challenges in section type discovery.

Psychiatric evaluations include long-form unstructured text. They are the end product of an assessment in which a psychiatrist summarizes the information they have gathered, integrating the patient history, evaluation, diagnosis, and suggested treatments or future steps (see, e.g., Groth-Marnat, Handbook of Psychological Assessment, John Wiley & Sons, Hoboken, N.J., 2009; and Goldfinger et al., Psychological Assessment and Report Writing, Sage, Thousand Oaks, Calif., 2013; both of which are hereby incorporated by reference herein in their entireties). Although there is no strict format, there are general guidelines for writing these reports, typically structured as an ordered list of headed sections (see, e.g., American Psychiatric Association, American Psychiatric Association Practice Guidelines for the Treatment of Psychiatric Disorders: Compendium 2006, American Psychiatric Association Publishing, Washington, D.C., 2006; which is hereby incorporated by reference herein in its entirety).

In the examples, a corpus of psychiatric evaluations and a corresponding ontology of section types previously collected and developed (see, e.g., Banisakher et al., Automatically detecting the position and type of psychiatric evaluation report sections, In Proceedings of the Ninth International Workshop on Health Text Mining and Information Analysis, pages 101-110, 2018; which is hereby incorporated by reference herein in its entirety) were used. The corpus contains 150 publicly available psychiatric evaluations collected by crawling the web and querying custom search engines. The reports in the corpus were anonymized samples of either real or synthetic psychiatric evaluations written and published for educational purposes. Each evaluation is complete, and adheres to the general writing guidelines for psychiatric evaluations discussed earlier (Banisakher et al., 2018, supra.). FIG. 3 lists the main section types in their usual order of appearance as well as how often they appear in the corpus.

A discharge summary is the final documentation of a hospital stay. These reports summarize the course of hospital treatment by listing the various events during hospitalization (see, e.g., Horwitz et al., Comprehensive quality of discharge summaries at an academic medical center, Journal of hospital medicine, 8(8):436-443, 2013; which is hereby incorporated by reference herein in its entirety). Similar to psychiatric evaluations, discharge summaries are governed by general writing guidelines that suggest the information that should be included. In practice, different hospital networks and even different medical professionals within the same hospital often write these reports differently, tailoring them to specific patient cases.

A group of 150 discharge summaries was randomly extracted from the MIMIC-III database (Johnson et al., Mimic-iii, a freely accessible critical care database, Scientific Data, 3:160035-160035, 2016; which is hereby incorporated by reference herein in its entirety). Summaries that were complete and that adhered to the general clinical note writing guidelines were selected. As with all MIMIC-III data, the summaries are anonymized. An ontology of section types (see, e.g., Tepper et al., Statistical section segmentation in free-text clinical records, In Proceedings of the Eighth International Conference on Language Resources and Evaluation (LREC-2012), pages 2001-2008, 2012; which is hereby incorporated by reference herein in its entirety) was selected and used. FIG. 5 lists the main section types in their usual order of appearance as well as how often they occur in the corpus.

A radiology report is a summary of a radiology scan, such as an X-Ray scan or a magnetic resonance imaging (MRI) scan, where a radiologist communicates findings and an analysis of the results (The American Board of Radiology (ABR), as of Apr. 27, 2019). Similar to psychiatric evaluations and discharge summaries, radiologists are typically trained to follow a general guideline. This is not a strict format, as reports vary in their section structure and content based on the procedure performed, the patient's specific case, and the radiologist's and medical institution's writing styles. Similar to discharge summaries, 423 radiology reports were randomly extracted from MIMIC-III (Johnson et al., 2016, supra.) that were complete and adhered to the general radiology writing guidelines (ABR, 2019). These reports covered a variety of procedures and scan types, including X-Ray, MRI, and ultrasound scans. An ontology of section types (see Tepper et al., 2012, supra.) was selected and used. FIG. 4 lists the main section types in their usual order of appearance as well as how often they occur in the corpus.

Patents are the result of a successful patent application, and published patent applications show the publication of a previous or in-progress application. Many of a patent's sections are mandatory (e.g., the claims section). Similarly, the description section in these documents is further composed of subsections, some of which are mandatory, while others are optional and can depend on the inventors, the authoring agent or attorney, and/or the patent's technical topics. Patent section segmentation can be done such that the structure of the description section in a patent document is outlined into five mandatory and two optional segments (see, e.g., Brugmann et al., Towards content-oriented patent document processing: intelligent patent analysis and summarization, World Patent Information, 40:30-42, 2015; which is hereby incorporated by reference herein in its entirety).

In the examples, the description section of patent documents was focused on and can be referred to as "patent documents" or "a patent document" in the examples, even though it does not include the figures, the claims, or some other sections that might otherwise be present. A group of 464 U.S. patent documents was randomly collected using the PATENTSCOPE database provided by the World Intellectual Property Organization (WIPO). The documents spanned the period between 1954 and 2010. The description sections were then extracted from the original patent documents to construct the corpus. An ontology of section types (see Brugmann et al., 2015, supra.) was selected and used. FIG. 6 lists the main section types in their usual order of appearance as well as how often they occur in the corpus.

There are several challenges in discovering section types within a given document class. First, there is great ambiguity and variety in the section headings present in the data (see, e.g., Banisakher et al., 2018, supra.; and Li et al., Section classification in clinical notes using supervised hidden markov model, In Proceedings of the 1st ACM International Health Informatics Symposium IHI, pages 744-750, Arlington, Va., 2010; which is hereby incorporated by reference herein in its entirety). Using psychiatric reports as an example, a section labeled "Identification of Patient" by one psychiatrist might be labeled "Referral Data" or "Identifying Information" by another. Second, some sections are included inside others; for example, the section "Medical History" might include "Review of Symptoms" and/or "Psychiatric History" subsections, while the section "Family History" might include a subsection addressing "Pregnancy". Like sections, these subsections can either be explicitly labeled (heading present) or just implicit (heading omitted). Third, the section ordering can differ between reports, again, depending on the psychiatrist. Fourth, sections may be omitted, especially when that information is not relevant to the patient in question. For example, a report regarding a male patient would likely not contain a "Pregnancy" section. These challenges apply equally to many other types of clinical reports, including but not limited to discharge summaries and radiology reports.

Some document classes have stricter expectations about section structure than others. For example, while patent documents are more uniformly structured than clinical documents, they still suffer from inconsistencies between different authors, and especially among different countries. In an effort to minimize these inconsistencies and to increase interoperability of patent analysis and discovery systems, WIPO outlined writing guidelines for patent documents in its patent drafting manual (WIPO Patent Drafting Manual, World Intellectual Property Organization, Geneva, Switzerland, 2007). Even so, the manual itself discusses and accepts the possibility of different formatting and structuring of the sections of full patent documents. Thus, the challenges outlined above for clinical documents also apply (perhaps to a lesser degree) to U.S. patent documents.

Embodiments of the subject invention can overcome the above-listed challenges. Given a corpus of documents from a single document class (e.g., psychiatric reports), embodiments can identify a section structure that reflects the underlying statistics of the corpus. That is, a distinct list and general order of section types can be identified regardless of the section labels found within the documents. For example, a section originally labeled as "Identifying Data" by one psychiatrist and "Identification of Patient" by another, in two different reports, can be identified as a single distinct section type.

In many embodiments, systems and methods can use an approach that treats the identification as a Bayesian model merging problem. The ASM approach, which applies model merging to natural language text, can be used. In the ASM approach, events can correspond to model states, and deriving the clustering can involve four steps: (1) creating an initial model incorporating the sequence of events in each document in the corpus; (2) defining a merge operation over the events; (3) defining a prior over the models created; and (4) searching the merge space. The event clustering task is analogous to section discovery, where events are replaced by sections.

In the approach to section discovery/determination/identification, the ASM steps for events can be adapted and extended. Given a corpus, an initial Hidden Markov Model (HMM)-like model can be created, where each document is represented as a linear chain of states, with each state corresponding to a section of unknown type in the same order as found in the document. For example, a document containing ten sections can be represented with a chain of ten states. Thus, for 150 reports in a psychiatric reports corpus, for example, it can start with 150 linear branches including states that represent the sections. The model can also incorporate single start and end states that link to all the first and last states of each of the linear branches, respectively. A goal in the approach is to iteratively merge similar section states, maximizing the posterior probability P(M|D), the probability of a model given the data, for each model P($M_i$), where 1≤i≤N, and N is the total number of models processed. N grows as the solution proceeds, reaching the maximum model probability. FIG. 1 shows an example of this approach. The next three steps are a merge operation, defining the prior over linear models, and the similarity function, which will now each be described in more detail.

The merge operation merges two states in one model to generate a new model. The states' content are represented as bigram models of the free text of their corresponding section(s). A merged state's emission and transition probabilities are obtained from the weighted sum of their parent states, thus modeling the order of section types. Two restrictions can be added on candidate merged models. First, no cycles are allowed in a merged model, which maintains a directed order of sections and disallows repeated section types in a single linear chain. Second, only sections with section-to-document-size ratios with one standard deviation of each other may be merged. This ratio (section-to-document-size ratio) is the number of tokens in a section to the number of tokens in the document. The rationale for this restriction is that, given a document class, there is a general expectation on the size of a specific section type relative to its document size. In scientific articles, for example, an introduction section in an eight-page long scientific article is typically about a page long while it would be two to three pages long in a 30 or 40 page article. Placing this as a restriction on the model rather than a weight can be seen as favoring precision over recall as models with states containing more similar sections are favored.

After the search converges to a model with maximum probability, the most likely label (header) for each state can be obtained by computing a majority vote over the headers of the sections merged into that state. The approach can thus be further used to identify actual section headers for a document class in a given corpus.

With respect to defining the prior over linear models, the posterior probability guides the search in model merging, but a prior probability is needed to compute it. A prior probability distribution represents the initial belief over the size and structure of the models. First a normal distribution over the number of sections present in the model is assumed. For instance, in clinical notes this follows intuition in that: (1) patients share similar characteristics overall; (2) most patients treated fall under an umbrella of a small subset of medical issues (e.g., depression, anxiety, and ADHD in mental health); and (3) most medical professionals share a similar report writing and structuring style given that they follow the general medical writing guidelines. A similar intuition follows for patent documents as well. This intuition was verified through examination of the corpora, as in the examples.

Additionally, models that merge states with dissimilar content can be disallowed. This can be achieved by setting a similarity threshold and setting the prior probability to zero if a state merges two sections with content less than a threshold T. The similarity function is defined below. The resulting prior P(M) is thus formulated as follows:

$$P(M) = N(\mu, \sigma^2) \prod_i G(S_i) \quad (1)$$

$$G(S_i) = \begin{cases} 1 & \forall s_j, s_k \in S_i, \text{Sim}(s_j, s_k) > T \\ 0 & \text{otherwise} \end{cases} \quad (2)$$

In Equation 1, the normal distribution N($\mu$, $\sigma^2$) is multiplied by the product of a threshold function for each state in the model M. $S_i$ is the $i^{th}$ state in M. In Equation 2, $s_j$ and $s_k$ are section contents (i.e., text blocks) that have been merged into state $S_i$, Sim is the similarity function, and T is a similarity threshold. For a strict similarity threshold T is set to be 1.5 standard deviation from the mean similarity of all candidate sections to be merged, and therefore is tuned to the data.

The similarity function Sim takes the content of two candidate sections $s_j$ and $s_k$ (or collection of sections in the case of merged states), and computes the cosine similarity of their vector representations. These vector representations are computed from a set of extracted features that are used to model a section's free text content. The following sets of lexical, positional, and semantic features can be extracted: (1) unigrams and bigrams; (2) the top three key terms per section as indicated by tf-idf (Church et al., Inverse document frequency (idf): A measure of deviations from Poisson, In Natural Language Processing Using Very Large Corpora, pages 283-295, Springer, New York, 1999; which is hereby incorporated herein by reference in its entirety); (3) the section position relative to its document; (4) the length of the section in tokens; (5) extracted named entities, their types, and counts; and (6) the Wu-Palmer similarity score (Wu et al., Verbs semantics and lexical selection, In Proceedings of the 32nd annual meeting on Association for Computational Linguistics, pages 133-138, Association for Computational Linguistics, 1994; which is hereby incorporated herein by reference in its entirety). Additionally, although not shown in Equation 2, if the headers of all sections in the merged states are exactly the same, G($S_i$) is set to 1.

With respect to searching the merge space, the posterior probability P(M|D) drives the search, as maximizing it will result in a generalizable model that fits the given data. Greedy, best-first search can be used (e.g., because of the size of the merge space). P(M|D) need not be computed directly, but P(M)P(D|M) can be computed, and that is proportional to P(M|D). Further, because computing P(D|M) is costly, it can be estimated following approximations that compute heuristics for finding a maximum a posteriori probability (MAP) (see also, e.g., Stolcke et al., Hidden markov model induction by bayesian model merging, In Advances in neural information processing systems, pages 11-18, 1993; which is hereby incorporated by reference herein in its entirety).

FIG. 1 shows an example of the section merging approach, according to an embodiment of the subject invention, over two small psychiatric reports. Each psychiatric report comprises four sections: "Identifying Data", "Review of Symptoms", "Pregnancy", and "Treatment" in the first report, and "Patient", "Education", "Medical History", and "Plan Formulation" in the second. In the first model $M_0$, the model is initialized such that each report is an HMM-like linear chain of states that in turn correspond to sections in their original order of appearance. FIG. 1 shows a series of merges leading to the model that maximizes the posterior under the described parameters. In $M_1$, "Identifying Data" and "Patient" are merged into a single state, and the transitions are inherited as well as the section headers and content. Similarly, this is shown for "Review of Symptoms" and "Medical History" in $M_2$, and for the last two sections in each report in $M_3$. The final model $M_3$ can generate not only the two input reports (i.e., two distinct section sequences), but an additional two section sequences that alternatively include or exclude both states 3 and 6. Thus, the model can generalize beyond the two input examples. Most importantly, a distinct list of section types and ordering for the input data can be obtained from the generalizing final model.

There are no known related art systems or methods to automatically discover section types in documents. The output model in embodiments of the subject invention can contain a distinct list of section types (i.e., an ontology). In ontology learning and extraction, however, there no related art systems or methods can learn the section structure of a document. Instead, related art approaches focus on learning semantic concepts and relations, often using the document structure as input that is known ahead of time.

In many embodiments, the section boundaries should be known ahead of time (before the analysis to determine section types is performed). Modifying the approach to operate on the sentence level could conceivably be done, and this could transform the approach into a complete section structure extraction system.

Labeling sections (e.g., Introduction, Methods, Conclusion, etc.) of documents, which is an important step in automatic document understanding, requires knowledge of the section types (e.g., what sections should be present, in what order, the various possible headings, and containing what kind of language). Systems and methods of embodiments of the subject invention can use an approach to automatically discover this knowledge for a document class in a data driven fashion using a modified Bayesian model merging algorithm. No related art approach exists for discovering class-specific section types that generalizes across a multitude of document classes; and no related art approach can automatically segment, as well as identify, specific sections for a domain-specific document, such as psychiatric evaluation reports. Embodiments of the subject invention can use an algorithm that is able to distinguish implicit section structure (i.e., sections included implicitly within other sections and under different headings). The algorithm can specifically solve the problem of automatically detecting the section label and structure in a domain-specific document. The algorithm is designed to learn the specific characteristics of a given dataset.

Embodiments of the subject invention can be used in, for example, programs that automatically analyze text. Embodiments are also useful in many natural language processing pipelines. The algorithms used with systems and methods of embodiments of the subject invention can learn the section structure for documents from an underlying dataset and can provide computers with knowledge about the specific features of the language used in a given dataset.

Embodiments of the subject invention can be used in several applications, including but not limited to electronic health record systems in hospitals and clinics, document search systems, automatic summarization systems, document analyzation systems, and automatic digitization systems that aid optical character recognition (OCR) systems for scanned documents. Also, the issue of inconsistent document structure in various domains (e.g., medical reports, Internal Revenue Service (IRS) documents, scientific articles, books, papers, news articles, etc.) is becoming a more pressing issue as there is an exponential growth in digital data. Many organizations are interested in processing and analyzing large numbers of documents that are inconsistent in structure, and the first step to processing such documents can be to use systems or methods of the subject invention that learn and detect the underlying document structure of every document.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the embodiments of the subject invention and of their many advantages may be had from the following examples, given by way of illustration.

The following examples are illustrative of some of the methods, applications, embodiments, and variants of the present invention. They are, of course, not to be considered as limiting the invention. Numerous changes and modifications can be made with respect to the invention.

Example 1

Systems and methods of embodiments of the subject invention utilize an approach that aims to identify a section structure that reflects the underlying statistics of the corpus. Thus, the output model can result in: (1) a set of pro-posed section types; and (2) a finite state machine modeling the order for those sections. In the examples, these two results can be evaluated separately. The ontologies discussed herein were used for the section types and used to annotate the corpora, and this ground truth (which was not provided to the models) was used for the evaluation. Additionally, section types were given a preferred label (header) following a majority vote of merged sections in each state.

In order to evaluate section type discovery (i.e., identifying the set of possible section types) it was treated as a document clustering task, with each section a separate document. The models of embodiments of the subject invention were compared against three document clustering baselines: K-means over tf-idf vectors; K-means over latent Dirichlet allocation (LDA) topic vectors; and Non-negative Matrix Factorization (NMF) using tf-idf vectors. Similar to previous experimental setups for K-means (Xie et al., In Proceedings of the Twenty-Ninth Conference on Uncertainty in Artificial Intelligence, pages 694-703, AUAI Press, 2013; which is hereby incorporated by reference herein in its entirety) and for NMF (Hosseini-Asl et al., Nonnegative matrix factorization for document clustering: A survey, In International Conference on Artificial Intelligence and Soft Computing, pages 726-737, Springer, 2014; which is hereby incorporated by reference herein in its entirety), these algorithms were provided with the correct number of clusters k for each corpus. This is not possible in the general case and therefore it would generally be expected that the results for K-means and NMF would be worse than shown here. Additionally, to maximize the performance of the baselines, clustering of sections within the same document was disallowed, as sections from the same document will often be grouped because they share similar topic and term distributions. The clustering was evaluated using two metrics: the chance-adjusted Rand index (Rand) to evaluate the overall clustering quality, and the $F_1$ measure to each section type independently. To evaluate the section ordering, an $F_1$ measure was computed for each section type that compared the proportions of succeeded sections in the model to that in the ground truth annotations.

The models and baselines were compared over the four corpora discussed herein (for psychiatric evaluations, discharge summaries, radiology reports, and patent documents). The approach of embodiments of the subject invention significantly outperformed all three baselines when discovering section types, with improvements of 78%, 107%, 61%, and 82%, respectively, for each corpus, over the best performing baseline (LDA+K-means). FIG. 7 shows these results. The Rand index is analogous to accuracy, which suggests that most states in the model of embodiments of the subject invention had a relatively small number of dissimilar sections.

Five feature combination experiments were also performed. Adding section positional and length features had a significant positive impact on the model's performance, achieving above 80% on the Rand index, while semantic features helped, but by a lower factor. Further, the impact of using exact header matching (see also the discussion herein on the merge operation) was tested by relaxing that rule. Under that condition, the models only lost 3% performance on average between all the corpora, which shows that the models of embodiments of the subject invention can be effective even when a corpus contains no section header information at all.

The approach of embodiments also significantly outperformed all baselines even when only using lexical features. Careful inspection of the baseline results revealed that sections were grouped based on topics—an expected result. For example, LDA-K-means created a cluster for ADHD in the psychiatric evaluations corpus and thus grouped sections regardless of type into that cluster. This confirms that topical models and classical document clustering techniques are inefficient in discriminating "types" of text rather than "topics".

Example 2

The models discussed in Example 1 were also evaluated for performance on each section type individually using precision, recall, and $F_1$ (see also FIGS. 3-6). Compared against ground truth, the models of embodiments of the subject invention performed significantly better for sections with highly distinctive content (than most other sections): e.g., "Diagnosis" in psychiatric evaluations, "Discharge Instructions" in discharge summaries, "Exam" in radiology reports, and "Description of Drawings" in patent documents. Similarly, the models of embodiments performed better in beginning and ending sections in general (e.g., "Treatment Plan" in psychiatric reports, and "Discharge Medications" in discharge summaries). It is speculated that this is because those sections typically display minimal variability in position. On average the precision was higher than recall reflecting the explicit choice to bias toward precision (see also the discussion herein with respect to defining the prior over linear models).

The confusion matrix was computed counting the correct (TP), incorrect (FP), and missing (FN) forward transitions for each section type in comparison with the ground truth annotation, and then these were used to compute the precision (P), recall (R), and $F_1$ scores. Average P, R, and $F_1$ were then obtained by weighing the scores by the number of sections for each section type (see FIG. 8). The model of embodiments of the subject invention achieved high performance for all four corpora, while again performing best on the patent corpus and achieving a 0.95 weighted $F_1$ score. This can be partially attributed to the fact that patent documents have a more uniform section structure compared to the other document classes.

Overall, the approach of embodiments of the subject invention performed best on patent documents, followed by the psychiatric and radiology corpora, and worst on discharge summaries. Analysis of the results and data can lead to characterizing the approach in four ways as the resulting models favor document classes with (1) higher variance in section content distinctiveness, (2) lower average section-to-document ratio, (3) higher average word-to-section ratio, and (4) more uniform ordering.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for determining section types of a given document class, the system comprising:
   a processor;
   a memory in operable communication with the processor; and
   a machine-readable medium in operable communication with the processor and the memory, the machine-readable medium having instructions stored thereon that, when executed by the processor, perform the following steps:
      receiving a corpus of documents of the given document class;
      using a modified Bayesian model merging algorithm on the corpus to determine the section types of the given document class; and
      storing the determined section types on the memory to be used for labeling a document of the given document class,
   the using of the modified Bayesian model merging algorithm on the corpus comprising:
      creating an initial Hidden Markov Model (HMM)-like model, where each document of the corpus is represented as a linear chain of states, with each state of the linear chain of states corresponding to a section of unknown type in a same order as found in the respective document of the corpus;
      performing a merge operation on the initial HMM-like model to merge states and generate an updated model;
      defining a prior probability distribution over the updated model;
      computing a posterior probability distribution based on the prior probability distribution; and
      searching a merge space of the updated model based on the posterior probability distribution to determine the section types of the given document class.

2. The system according to claim 1, the using of the modified Bayesian model merging algorithm on the corpus comprising extending an analogical story merging (ASM) approach with a Bayesian model merging algorithm.

3. The system according to claim 1, the searching of the merge space of the updated model comprising maximizing the posterior probability distribution to give a generalizable model that fits the corpus.

4. The system according to claim 1, the computing of the posterior probability distribution comprising computing P(M)P(D|M), which is proportional to P(M|D),
   where P(M) is the prior probability distribution, P(M|D) is the posterior probability distribution, M represents the updated model, and D represents a document of the corpus.

5. The system according to claim 1, the defining of the prior probability distribution comprising using the following equations $$P(M) = N(\mu, \sigma^2) \prod_i G(S_i)$$

$$G(S_i) = \begin{cases} 1 & \forall\ s_j, s_k \in S_i, \text{Sim}(s_j, s_k) > T \\ 0 & \text{otherwise} \end{cases},$$

where P(M) is the prior probability distribution, M represents the updated model, $N(\mu, \sigma^2)$ is a normal distribution of the updated model, $S_i$ is the $i^{th}$ state in the updated model, $s_j$ and $s_k$ are section contents that have been merged into state $S_i$, Sim is a similarity function that takes content of $s_j$ and $s_k$ and computes a cosine similarity of vector representations of $s_j$ and $s_k$, and T is a similarity threshold.

6. The system according to claim 5, T being set as 1.5 standard deviations from a mean similarity of the similarity function.

7. The system according to claim 5, where, if headers of all sections in the updated model are exactly the same, G(Si) is set to 1.

8. The system according to claim 1, the corpus of documents comprising at least 100 documents.

9. The system according to claim 1, the given document class being a psychiatric evaluation, a discharge summary, a radiology report, or a United States patent document.

10. A method for determining section types of a given document class, the method comprising:
   receiving, by a processor, a corpus of documents of the given document class;
   using, by the processor, a modified Bayesian model merging algorithm on the corpus to determine the section types of the given document class; and
   storing, by the processor, the determined section types on a memory in operable communication with the processor to be used for labeling a document of the given document class,
   the using of the modified Bayesian model merging algorithm on the corpus comprising:
      creating an initial Hidden Markov Model (HMM)-like model, where each document of the corpus is represented as a linear chain of states, with each state of the linear chain of states corresponding to a section of unknown type in a same order as found in the respective document of the corpus;
      performing a merge operation on the initial HMM-like model to merge states and generate an updated model;
      defining a prior probability distribution over the updated model;
      computing a posterior probability distribution based on the prior probability distribution; and
      searching a merge space of the updated model based on the posterior probability distribution to determine the section types of the given document class.

11. The method according to claim 10, the using of the modified Bayesian model merging algorithm on the corpus comprising extending an analogical story merging (ASM) approach with a Bayesian model merging algorithm.

12. The method according to claim 10, the searching of the merge space of the updated model comprising maximizing the posterior probability distribution to give a generalizable model that fits the corpus.

13. The method according to claim 10, the computing of the posterior probability distribution comprising computing P(M)P(D|M), which is proportional to P(M|D),
   where P(M) is the prior probability distribution, P(M|D) is the posterior probability distribution, M represents the updated model, and D represents a document of the corpus.

14. The method according to claim 10, the defining of the prior probability distribution comprising using the following equations $$P(M) = N(\mu, \sigma^2) \prod_i G(S_i)$$

$$G(S_i) = \begin{cases} 1 & \forall s_j, s_k \in S_i, \text{Sim}(s_j, s_k) > T \\ 0 & \text{otherwise} \end{cases},$$

where P(M) is the prior probability distribution, M represents the updated model, $N(\mu, \sigma^2)$ is a normal distribution of the updated model, $S_i$ is the $i^{th}$ state in the updated model, $s_j$ and $s_k$ are section contents that have been merged into state $S_i$, Sim is a similarity function that takes content of $s_j$ and $s_k$ and computes a cosine similarity of vector representations of $s_j$ and $s_k$, and T is a similarity threshold.

15. The method according to claim 14, T being set as 1.5 standard deviations from a mean similarity of the similarity function.

16. The method according to claim 14, where, if headers of all sections in the updated model are exactly the same, G(Si) is set to 1.

17. The method according to claim 10, the corpus of documents comprising at least 100 documents.

18. A system for determining section types of a given document class, the system comprising:
a processor;
a memory in operable communication with the processor; and
a machine-readable medium in operable communication with the processor and the memory, the machine-readable medium having instructions stored thereon that, when executed by the processor, perform the following steps:
receiving a corpus of documents of the given document class;
using a modified Bayesian model merging algorithm on the corpus to determine the section types of the given document class; and
storing the determined section types on the memory to be used for labeling a document of the given document class,
the using of the modified Bayesian model merging algorithm on the corpus comprising:
creating an initial Hidden Markov Model (HMM)-like model, where each document of the corpus is represented as a linear chain of states, with each state of the linear chain of states corresponding to a section of unknown type in a same order as found in the respective document of the corpus;
performing a merge operation on the initial HMM-like model to merge states and generate an updated model;
defining a prior probability distribution over the updated model;
computing a posterior probability distribution based on the prior probability distribution; and
searching a merge space of the updated model based on the posterior probability distribution to determine the section types of the given document class,
the searching of the merge space of the updated model comprising maximizing the posterior probability distribution to give a generalizable model that fits the corpus,
the computing of the posterior probability distribution comprising computing P(M)P(D|M), which is proportional to P(M|D),
where P(M) is the prior probability distribution, P(M|D) is the posterior probability distribution, M represents the updated model, and D represents a document of the corpus,
the defining of the prior probability distribution comprising using the following equations $$P(M) = N(\mu, \sigma^2) \prod_i G(S_i)$$

$$G(S_i) = \begin{cases} 1 & \forall s_j, s_k \in S_i, \text{Sim}(s_j, s_k) > T \\ 0 & \text{otherwise} \end{cases},$$

where $N(\mu, \sigma^2)$ is a normal distribution of the updated model, $S_i$ is the $i^{th}$ state in the updated model, $s_j$ and $s_k$ are section contents that have been merged into state $S_i$, Sim is a similarity function that takes content of $s_j$ and $s_k$ and computes a cosine similarity of vector representations of $s_j$ and $s_k$, and T is a similarity threshold,
T being set as 1.5 standard deviations from a mean similarity of the similarity function,
where, if headers of all sections in the updated model are exactly the same, G(Si) is set to 1,
the corpus of documents comprising at least 100 documents, and
the given document class being a psychiatric evaluation, a discharge summary, a radiology report, or a United States patent document.

* * * * *